(12) United States Patent
Khalaj Amineh et al.

(10) Patent No.: US 9,562,877 B2
(45) Date of Patent: Feb. 7, 2017

(54) EVALUATION TOOL FOR CONCENTRIC WELLBORE CASINGS

(71) Applicant: HALLIBURTON ENERGY SERVICES, INC., Houston, TX (US)

(72) Inventors: Reza Khalaj Amineh, Houston, TX (US); Luis Emilio San Martin, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/026,194

(22) PCT Filed: Jul. 10, 2015

(86) PCT No.: PCT/US2015/039990
§ 371 (c)(1),
(2) Date: Mar. 30, 2016

(87) PCT Pub. No.: WO2016/007883
PCT Pub. Date: Jan. 14, 2016

(65) Prior Publication Data
US 2016/0245779 A1  Aug. 25, 2016

Related U.S. Application Data

(60) Provisional application No. 62/023,762, filed on Jul. 11, 2014.

(51) Int. Cl.
*G01N 27/82* (2006.01)
*E21B 47/00* (2012.01)
(Continued)

(52) U.S. Cl.
CPC ............... *G01N 27/82* (2013.01); *E21B 47/00* (2013.01); *E21B 17/00* (2013.01); *G01V 3/28* (2013.01)

(58) Field of Classification Search
CPC ...... G01N 27/82; G01N 27/9033; G01V 3/28; G01V 3/30; G01V 3/38
(Continued)

(56) References Cited

U.S. PATENT DOCUMENTS 3,609,531 A * 9/1971 Forster ................. G01N 27/904
324/227
3,940,689 A  2/1976 Johnson, Jr.
(Continued)

OTHER PUBLICATIONS

International Search Report and Written Opinion issued in related PCT Application No. PCT/US2015/039990, mailed on Sep. 25, 2015 (10 pages).
(Continued)

*Primary Examiner* — Reena Aurora
(74) *Attorney, Agent, or Firm* — Scott Richardson; Baker Botts L.L.P.

(57) ABSTRACT

A system comprises one or more first electromagnetic coils configured to generate and direct first excitation signals toward a plurality of casings in a wellbore and receive response signals based on the excitation signals. The system also comprises a magnetic field source configured to generate a static magnetic field in a particular casing of the plurality of casings and a magnetometer configured to receive response signals based on the static magnetic field in the particular casing. The system further comprises one or more processors configured to receive a first response signal from the one or more electromagnetic coils, receive a second response signal from the magnetometer, and determine, based on the first response signal and the second response signal, whether a defect exists in the plurality of casings.

42 Claims, 6 Drawing Sheets

(51) Int. Cl.
*G01V 3/28* (2006.01)
*E21B 17/00* (2006.01)

(58) Field of Classification Search
USPC .................................................. 324/232, 242
See application file for complete search history.

(56) References Cited

U.S. PATENT DOCUMENTS

| | | | |
|---|---|---|---|
| 4,602,212 | A | 7/1986 | Hiroshima et al. |
| 5,446,382 | A | 8/1995 | Flora |
| 5,461,313 | A | 10/1995 | Bohon et al. |
| 2009/0101337 | A1* | 4/2009 | Neidhardt ............... E21B 47/08 |
| | | | 166/250.01 |
| 2009/0195244 | A1 | 8/2009 | Mouget et al. |
| 2011/0167914 | A1 | 7/2011 | Sutherland |
| 2013/0193953 | A1 | 8/2013 | Yarbro et al. |

OTHER PUBLICATIONS

Garcia, J. et al., "Successful Application of a New Electromagnetic Corrosion Tool for Well Integrity Evaluation in Old Wells Completed with Reduced Diameter Tubular," In IPTC 2013: International Petroleum Technology Conference. Mar. 2013.
Arbuzov, A.A., "Memory magnetic imaging defectoscopy," in SPE Russian Oil and Gas Exploration and Production Technical Conference and Exhibition. Society of Petroleum Engineers Paper 162054. Jan. 2012.

* cited by examiner

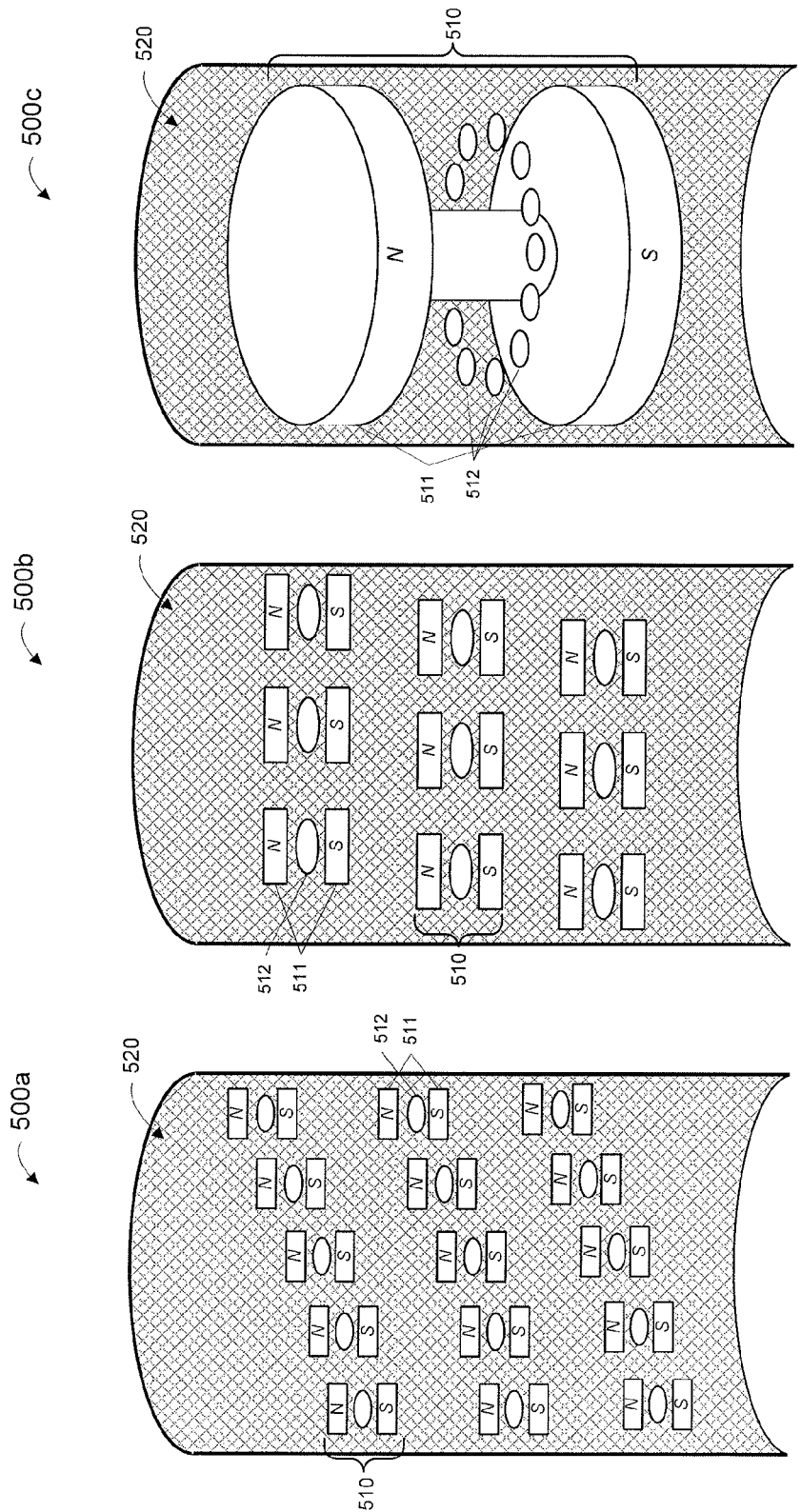

EVALUATION TOOL FOR CONCENTRIC WELLBORE CASINGS

CROSS-REFERENCE TO RELATED APPLICATIONS

The present application is a U.S. National Stage Application of International Application No. PCT/US2015/039990 filed Jul. 10, 2015, which claims priority to U.S. Provisional Patent Application No. 62/023,762 filed Jul. 11, 2014, both of which are incorporated herein by reference in their entirety for all purposes.

BACKGROUND

This disclosure generally relates to wellbore casing evaluation. In particular, this disclosure relates to systems and methods for evaluating multiple concentric wellbore casings using combinations of eddy current (EC), magnetic flux leakage (MFL), and electromagnetic acoustic transducer (EMAT) techniques.

Hydrocarbons, such as oil and gas, are commonly obtained from wellbores in subterranean formations located onshore or offshore. During operations, the condition of the wellbore casing may deteriorate with one or more defects appearing in the wellbore casing. The defects may be caused by corrosion or other factors, and such defects may make wellbore operations inefficient, may hinder production from the wellbore, or may damage the environment. Current methods of wellbore casing analysis may include casing removal, which may be both expensive and time consuming, particularly in offshore platforms.

BRIEF DESCRIPTION OF THE DRAWINGS

These drawings illustrate certain aspects of certain embodiments of the present disclosure. They should not be used to limit or define the disclosure.

FIGS. 5A-5C illustrate example configurations of casing evaluation tools in accordance with embodiments of the present disclosure;

Figure 1:
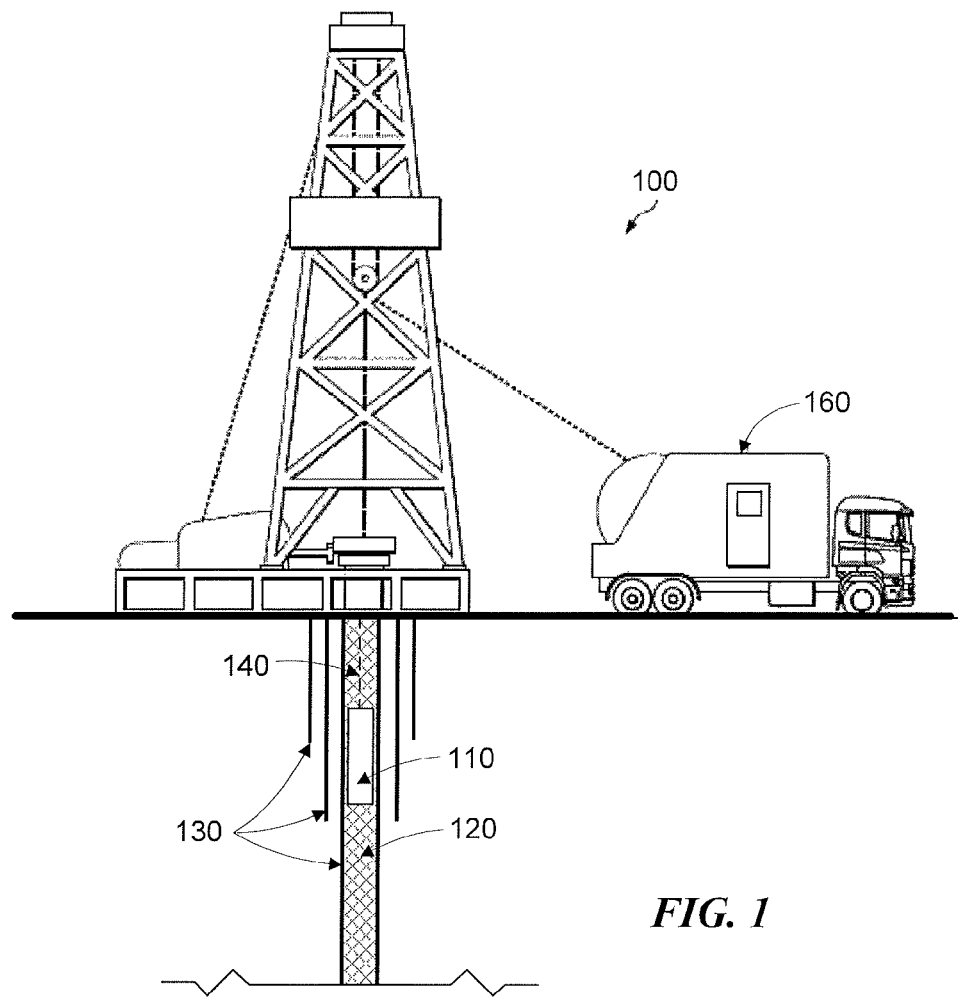
FIG. 1 illustrates an example downhole logging system used in a hydrocarbon drilling environment in accordance with embodiments of the present disclosure.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure describes systems and methods for performing evaluations of multiple, concentric wellbore casings using combinations of eddy current (EC), magnetic flux leakage (MFL), and electromagnetic acoustic transducer (EMAT) techniques. In particular, the present disclosure describes systems and methods that utilize MFL, EMAT, and/or EC techniques for evaluating an inner casing of a plurality of casings, and EC techniques for measuring the outer casings of the plurality of casings. In certain embodiments, for instance, an eddy current excitation signal may be directed toward the plurality of casings, along with a second MFL or EMAT excitation signal. Responses to the excitation signals may be analyzed to determine whether defects exist in one or more of the casings. For example, the MFL/EMAT response signal may be analyzed to determine whether defects exist in the inner casing, while the EC response signal may be analyzed to determine whether defects exist in the outer casings.

Using the techniques described herein, multiple wellbore casings may be more accurately monitored for defects without requiring removal of the casings for inspection. In addition, defects in the wellbore casings may be more accurately distinguished from one another (e.g., distinguishing between defects on the same casing and between defects on different casings). Furthermore, accurate estimates of the inner-most casing's condition may be determined, which is important in monitoring multiple casings since better evaluation of the inner-most wellbore casing leads to better evaluation of the other outer wellbore casings as well.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the wellbore below), or otherwise nonlinear wellbores in any type of subterranean formation. Certain embodiments may be applicable, for example, to logging data acquired with wireline, slickline, and logging while drilling/measurement while drilling (LWD/MWD). Certain embodiments may be applicable to subsea and/or deep sea wellbores. Embodiments described below with respect to one implementation are not intended to be limiting.

FIG. 1 illustrates an example downhole logging system 100 used in a hydrocarbon drilling environment in accordance with embodiments of the present disclosure. Operations in a wellbore (e.g., logging or other data collection) may be conducted using downhole inspection tool 110 when some or all of a drill string has been removed from the wellbore. Downhole inspection tool 110 may include one or more logging tools (e.g., casing evaluation tools) that may be suspended into wellbore 120 (which may be formed by multiple casings 130) by cable 140 (e.g., wireline, slickline, or coiled tubing). Downhole inspection tool 110 may be communicatively coupled to cable 140, which may contain conductors for transporting power to downhole inspection tool 110 and signals from logging tools included therein to logging facility 160. However, cable 140 may alternatively lack a conductor, as is often the case using slickline or coiled tubing. Logging facility 160 (shown in FIG. 1 as a truck, although it may be any other structure) may collect measurements from downhole inspection tool 110, and may include computing facilities for controlling, processing, or storing the measurements communicated thereto. The computing facilities may be communicatively coupled to the components of downhole logging system 100 through any suitable means. An example computing facility is described further below with reference to computing system 200 of FIG. 2.

Modifications, additions, or omissions may be made to FIG. 1 without departing from the scope of the present disclosure. For example, FIG. 1 illustrates components of downhole logging system 100 in a particular configuration. However, any suitable configuration of components for logging a wellbore may be used. Furthermore, fewer components or additional components beyond those illustrated may be included in downhole logging system 100 without departing from the scope of the present disclosure.

Figure 2:
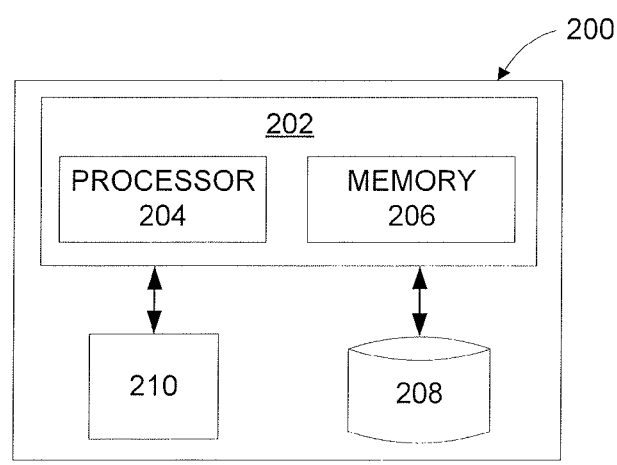
FIG. 2 illustrates a block diagram of an exemplary computing system for use in a downhole logging system in accordance with embodiments of the present disclosure.

FIG. 2 illustrates a block diagram of an exemplary computing system 200 for use in a downhole logging system in accordance with embodiments of the present disclosure. Computing system 200 or components thereof can be located at the surface (e.g., in logging facility 160), downhole (e.g., in downhole inspection tool 110), or some combination of both locations (e.g., certain components may be disposed at the surface while certain other components may be disposed downhole, with the surface components being communicatively coupled to the downhole components). Computing system 200 may be configured to generate excitation signals in EC, MFL, and/or EMAT sensors and analyze responses thereto to determine whether defects exist in wellbore casings, in accordance with the teachings of the present disclosure. For example, computing system 200 may be configured to perform the steps of the methods described below with respect to FIG. 7.

Computing system 200 may include casing evaluation module 202, which includes any suitable components. For example, in some embodiments, casing evaluation module 202 may include a processor 204 communicatively coupled to a memory 206. Processor 204 may include, for example a microprocessor, microcontroller, digital signal processor (DSP), application specific integrated circuit (ASIC), or any other digital or analog circuitry configured to interpret and/or execute program instructions and/or process data. Processor 204 may be configured to interpret and/or execute program instructions or other data retrieved and stored in memory 206. Program instructions or other data may constitute portions of software 208 for carrying out one or more methods described herein. Memory 206 may include any system, device, or apparatus configured to hold and/or house one or more memory modules; for example, memory 206 may include read-only memory, random access memory, solid state memory, or disk-based memory. Each memory module may include any system, device or apparatus configured to retain program instructions and/or data for a period of time (e.g., computer-readable non-transitory media). For example, instructions from software 208 may be retrieved and stored in memory 206 for execution by processor 204. Casing evaluation module 202 may be communicatively coupled to one or more displays 210 (e.g., located in logging facilities 160 of FIG. 1) such that information processed by casing evaluation module 202 may be conveyed to operators of the downhole logging system. For example, casing evaluation module 202 may convey results of defect evaluation methods of the present disclosure to display 210 for viewing by an operator of downhole inspection tool 110 of FIG. 1.

Modifications, additions, or omissions may be made to FIG. 2 without departing from the scope of the present disclosure. For example, FIG. 2 shows a particular configuration of components of computing system 200. However, any suitable configurations of components may be used. For example, components of computing system 200 may be implemented either as physical or logical components. Furthermore, in some embodiments, functionality associated with components of computing system 200 may be implemented in special purpose circuits or components. In other embodiments, functionality associated with components of computing system 200 may be implemented in configurable general purpose circuit or components. For example, components of computing system 200 may be implemented by configured computer program instructions.

Figure 3:
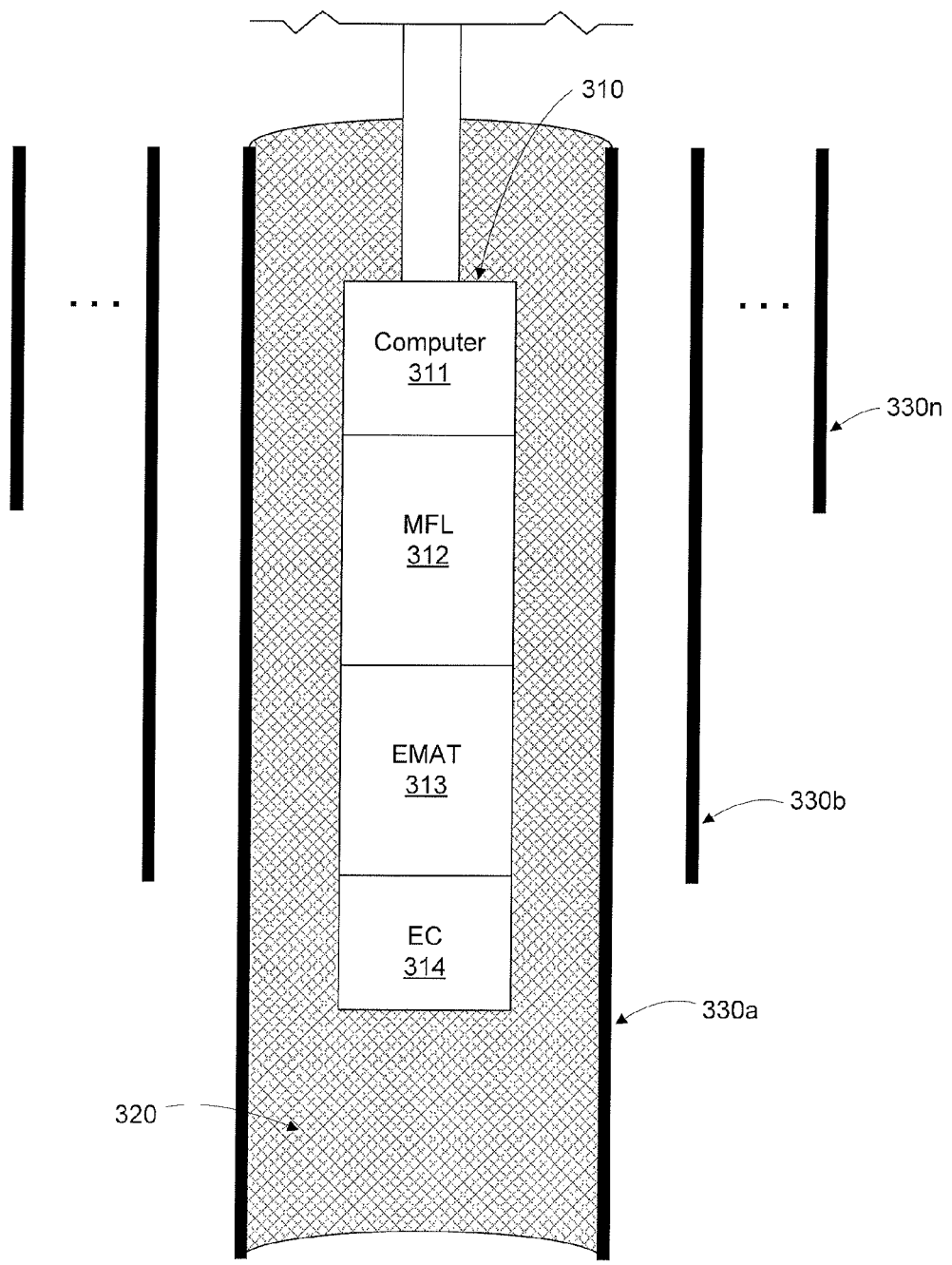
FIG. 3 illustrates a block diagram of an example casing evaluation tool in accordance with embodiments of the present disclosure.

FIG. 3 illustrates a block diagram of an example casing evaluation tool 310 in accordance with embodiments of the present disclosure. More particularly, FIG. 3 depicts a casing evaluation tool 310 that traverses a wellbore 320 comprising a plurality of concentric casings 330. Casing evaluation tool 310 may be a portion of a wireline system (e.g., downhole inspection tool 110 of FIG. 1), and may be configured to measure or provide information associated with casings 330 of wellbore 320. For example, casing evaluation tool may measure or provide estimates of the thickness of each casing 330, the degree of concentricity of casings 330, and/or other parameters associated with casings 330. Casing evaluation tool 310 comprises a computer 311 that may include, for example, a module for communication (e.g., to communicate measurements to a drilling operator uphole), a processor, memory, a battery, or any other suitable components. In some embodiments, computer 311 may comprises components similar to computing system 200 of FIG. 2.

Casing evaluation tool 310 further comprises magnetic flux leakage (MFL) sensor 312, electromagnetic acoustic transducer (EMAT) sensor 313, and eddy current (EC) sensor 314, which may each include any suitable hardware and/or software for performing its respective wellbore casing evaluation techniques (as described further below). For instance, MFL sensor 312 may include pick-up coils or Hall-effect sensors used as magnetometers for MFL techniques as described below, and EMAT sensor 313 may include a coil that generates an electromagnetic pulse towards the casing in the ultrasonic frequency range for EMAT techniques as described below. Example MFL and EMAT sensors are illustrated in and described below with respect to FIGS. 4A-4B, respectively, while associated configurations of such sensors are illustrated in and described below with respect to FIGS. 5A-5C. EC sensor 314 may include transmitter and receiver coils and excitation/data acquisition electronics to implement frequency-domain or time-domain (based on the pulsed eddy current) EC measurements as described below. In particular embodiments of the present disclosure, MFL and/or EMAT techniques may be employed for inspection of one casing (e.g., the innermost casing 330a) using MFL/EMAT sensor 313, while EC techniques may be employed for inspection of multiple casings (i.e., some or all of casings 330) using EC sensor 314.

Modifications, additions, or omissions may be made to FIG. 3 without departing from the scope of the present disclosure. For example, FIG. 3 shows a particular configuration of components of casing evaluation tool 310. However, any suitable configuration or combination of components may be used. For example, casing evaluation tool 310 may include multiple MFL sensors 312, EMAT sensors 313, or EC sensors 314. As another example, casing evaluation tool 310 may further include additional sensors for measuring downhole characteristics, such as temperature or pressure.

Figure 4A:
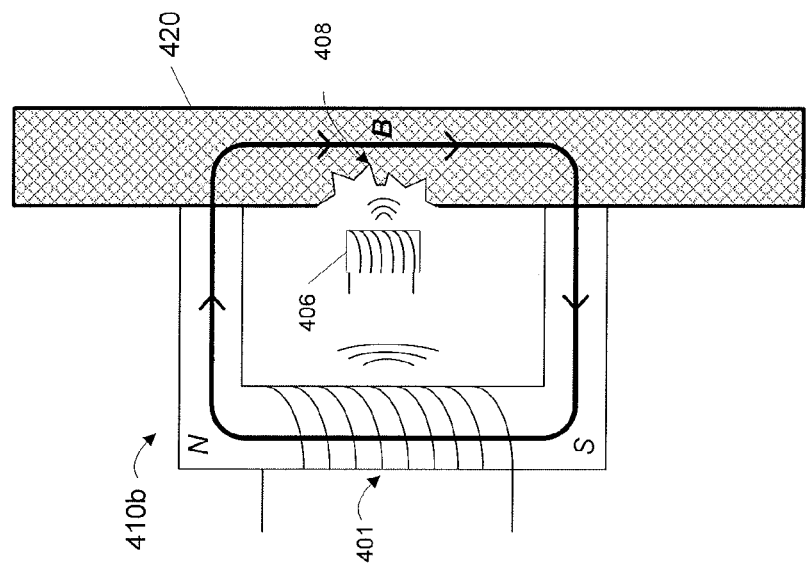
FIGS. 4A-4B illustrate example casing evaluation tools in accordance with embodiments of the present disclosure.
Figure 4B:
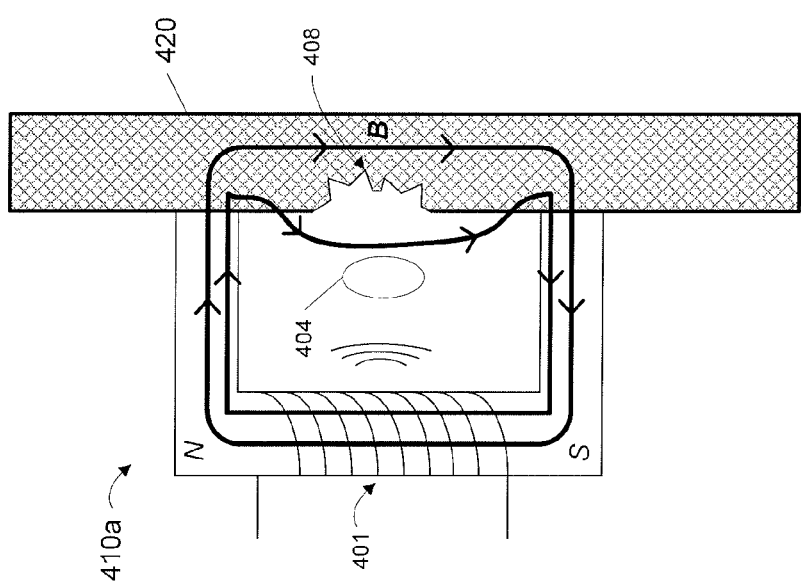

FIGS. 4A-4B illustrate example casing evaluation tools 410 in accordance with embodiments of the present disclosure. In particular, FIGS. 4A-4B illustrate example sensors that may be used in casing evaluation tools (e.g., casing evaluation tool 310 of FIG. 3 or logging tools of downhole inspection tool 110 of FIG. 1) for EC, MFL, and/or EMAT casing evaluation techniques in accordance with certain embodiments of the present disclosure. Each casing evaluation tool 410 includes a primary coil 401 coupled to wellbore casing 420. Primary coil 401 may be configured to generate and direct electromagnetic waves toward casing 420 in certain embodiments. Such electromagnetic waves are hereinafter referred to as excitation signals, and may be static or transient signals as described further below. In addition, primary coil 401 may be configured to generate a static magnetic field B inside casing 420 (as illustrated) in some embodiments. However, in other embodiments, a permanent magnet separate from primary coil 401 may be used to generate static magnetic field B inside casing 420. Furthermore, primary coil 401 may be configured to receive signals in response to the excitation signals, as described further below. Casing evaluation tools 410 may further include sensors, such as magnetometer 404 in FIG. 4A and secondary coil 406 in FIG. 4B, for detecting or measuring signals in response to excitation signals generated by primary coil 401 (and/or a permanent magnet in applicable embodiments) as described further below.

To implement EC casing evaluation techniques, primary coil 401 may generate transient electromagnetic fields, which generate eddy currents in casing 420. These eddy currents then produce secondary electromagnetic fields which are received by a receiver coil (which may be primary coil 401 or a dedicated receiver coil (not shown)). The data acquired by the receiver coil can be then employed to perform evaluation on multiple casings of a wellbore.

To implement MFL and/or EMAT casing evaluation techniques, a static magnetic field may be generated between two poles in casing 420 as shown in FIGS. 4A-4B. Static magnetic fields may travel inside casing 420 and close the magnetic circuit as shown in FIGS. 4A-4B. As discussed above, the static magnetic fields may be generated by primary coil 401 or by a permanent magnet.

In MFL evaluation techniques, defects such as defect 408 on casing 420 deflects the magnetic fields as shown in FIG. 4A, and disturbs the amount of magnetic field leakage to the air. These deflected magnetic fields may be detected by magnetometer 404 located in between the poles of the magnet generating the static magnetic field. Magnetometer 404 may include pick-up coils or Hall-effect sensors, in certain embodiments. Both radial and axial components of the deflected magnetic fields may be used as an indication of a defect, although their behavior may be different from one another. Large permanent magnets (or coils producing static magnetic field, such as coil 401) and an array of magnetometers (e.g., magnetometer 404) may be employed in certain embodiments to perform faster measurements without the need for fine mechanical sampling of casing 420. Example configurations are illustrated in and discussed further with respect to FIGS. 5A-5C.

In EMAT techniques, a secondary coil 406 may be located in proximity to the surface of casing 420, and may generate electromagnetic waves (e.g., an electromagnetic pulse) towards casing 420. Secondary coil 406 may include any suitable amount of coils, and may include a single coil for both transmitting and receiving signals or alternatively two coils (with the first being the transmitter and the second being the receiver). The spectral content of the generated pulse may be in the ultrasonic frequency range (100 KHz-10 MHz) in some embodiments. The electromagnetic wave may interact with casing 420 and generate ultrasonic waves via Lorentz force, Magnetization forces, or Magnetostriction due to piezo-magnetic effect. The ultrasonic waves may propagate in the material of casing 420 and reflect from the opposite end of casing 420, returning to the vicinity of secondary coil 406 after reflecting back. Reflected ultrasonic waves in the vicinity of the coil 406 may generate reflected electromagnetic waves by reverse operation of the above three mechanisms (i.e., Lorentz, Magnetization, and Magnetostriction). The reflected electromagnetic waves may be detected by secondary coil 406, and may then be separated out from detected eddy currents, flux leakage signals, and/or excitation fields by appropriate frequency and time filtering. The time of flight of the reflected electromagnetic waves detected by secondary coil 406 may provide a direct measurement of the width of casing 420. Large permanent magnets (or coils producing static magnetic field, such as primary coil 401) and an array of smaller transmitter/receiver coils (e.g., secondary coil 406) can be employed in certain embodiments to perform faster measurements without the need for fine mechanical sampling of casing 420. Example configurations are illustrated in and discussed further with respect to FIGS. 5A-5C.

Modifications, additions, or omissions may be made to FIGS. 4A-4B without departing from the scope of the present disclosure. For example, FIGS. 4A-4B show a particular configuration of components of casing evaluation tools 410. However, any suitable configuration or combination of components may be used. For example, casing evaluation tools 410 may include any suitable number of primary coils 401, magnetometers 404, or secondary coils 406, or any combination thereof for detecting or analyzing defects 408 in casing 420. FIGS. 5A-5C illustrate example configurations 500 of casing evaluation tools 510 in accordance with embodiments of the present disclosure. More particularly, FIGS. 5A-5C depict various configurations of casing evaluation tools 510 (comprising magnetizers 511 and sensors 512 (e.g., magnetometers or coils, such as magnetometer 404 of FIG. 4A and secondary coil 406 of FIG. 4B) for use with the MFL or EMAT techniques described above with respect to FIGS. 4A-4B. In the configuration shown in FIG. 5A, the sets of magnetizers 511 and sensors 512 are distributed in spiral configuration around the axis of casing 520. In the configuration shown in FIG. 5B, multiple sets of magnetizers 511 and sensors 512 are placed at axial positions along casing 520 and are staggered along the azimuthal direction. With configurations 500*a* and 500*b*, full azimuthal coverage can be achieved when the tool 510 is scanned along the axial direction. In certain embodiments, such as configuration 500*c* shown in FIG. 5C, the magnetic field can be produced by a large magnetizer 511. In such a configuration, sensors 512 may be distributed in the axial and/or azimuthal direction to sample the response signals. The magnetizer 511 may be one or more permanent magnets, one or more coils carrying DC current, or any suitable combination of the two. Furthermore, the coupling of the magnetic field to the casing wall can be performed via direct contact or via brushes with magnetic properties.

Modifications, additions, or omissions may be made to FIGS. 5A-5C without departing from the scope of the present disclosure. For example, FIGS. 5A-5C show particular configurations 500 of casing evaluation tools 510. However, any suitable configuration of casing evaluation tools 510 may be used.

Figure 6:
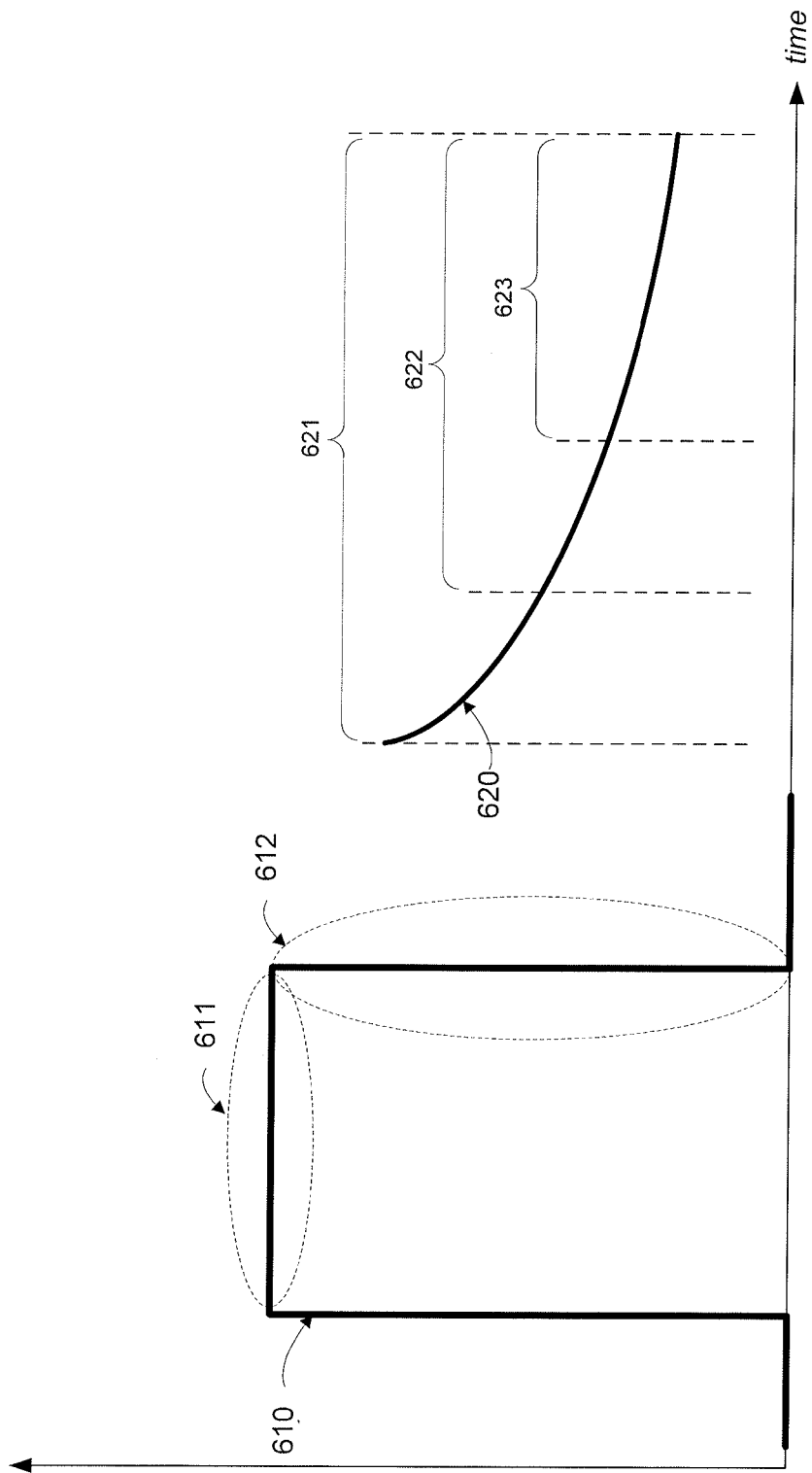
FIG. 6 illustrates an example excitation signal and associated response signal for casing evaluation tools in accordance with embodiments of the present disclosure.

FIG. 6 illustrates an example excitation signal 610 and associated response signal 620 for casing evaluation tools, in accordance with embodiments of the present disclosure. Excitation signal 610 includes a silent region 611 and an exciting edge 612. Response signal 620 may be divided into multiple regions 621-623, each of which may be associated with a different casing of a wellbore under evaluation. This is because when acquiring data for embodiments with multiple casings in the time domain, defects on the inner casings appear at earlier times in the response signal while defects on the outer casings appear in the response signal at longer decay times. The length in time of the response signal 620 may vary depending on the number of concentric casings in the wellbore and the dimensions of the wellbore configuration. As an example, and the response signal 620 may vary from 80 msec for embodiments with two concentric casings to hundreds of msec for embodiments with four concentric casings.

In embodiments employing a pulsed EC technique along with MFL or EMAT techniques, the coil used as the transmitter of excitation signal 610 (e.g., primary coil 401 of FIGS. 4A-4B) may be used as the magnetic field generator in the MFL or EMAT technique, as described above. In such embodiments, silent region 611 of excitation signal 610 may be employed to perform the static magnetic field measurements described above for the MFL and/or EMAT techniques. In other words, the MFL or EMAT technique measurements (or both) may be performed while a static magnetic field is generated during the silent region 611 of excitation signal 610, and the measurements for the EC techniques may be collected thereafter based on the response signal received based on exciting edge 612 of excitation signal 610 (i.e., the response received based on the transient electromagnetic signal generated by exciting edge 612).

In particular embodiments, data obtained through MFL techniques, EMAT techniques, or both may be employed to first evaluate the condition of the inner casing of multiple, concentric casings (e.g., casing 330a of FIG. 3), while data obtained through EC techniques may be employed to evaluate the condition of the outer casings of the multiple casings (e.g., casings 330b-n of FIG. 3). In such embodiments, a constrained inversion technique may be used to characterize the casings from the EC responses where inner casing thickness, conductivity, or magnetic permeability are constrained to be as close as possible to the estimations that are provided by the MFL and/or EMAT techniques. It is also possible that some range around the MFL and EMAT technique estimations is defined instead of fixing them to a specific value. Such a defined range may account for uncertainties in the MFL and EMAT measurements. A comparison between MFL and EMAT measurements can also be made to determine whether the defect is in the inner or outer surface of the inner casing, in particular embodiments.

In certain embodiments, data obtained through EC techniques may be combined with data obtained through MFL and/or EMAT techniques to evaluate the condition of the inner casing of the multiple casings. In such embodiments, the EC data may further be used to evaluate the outer casings, as previously described. In such embodiments, different regions 621-623 of response signal 620 may be associated with each of the casings. For example, data in region 621 of response signal 620 may be associated with the inner casing of the multiple casings (e.g., casing 330a of FIG. 3), data in region 622 of response signal 620 may be associated with the second casing of the multiple casings (e.g., casing 330b of FIG. 3), and data in region 623 of response signal 620 may be associated with a third casing of the multiple casings. Furthermore, shallow (i.e., higher frequency and lower listening time) readings of EC techniques may be used to maximize sensitivity of the readings with respect to the inner casing while minimizing sensitivity of the readings with respect to the outer casings. If both MFL and EMAT techniques are employed, as may be done in certain embodiments, each technique may use the same permanent magnet (or coil) as a source of static magnetic field.

Modifications, additions, or omissions may be made to FIG. 6 without departing from the scope of the present disclosure. For example, FIG. 6 shows a particular excitation signal 610 and response signal 620 associated with EC, MFL, and/or EMAT casing evaluation techniques. However, any suitable excitation signal or response signal may be used in performing such casing evaluation techniques.

Figure 7:
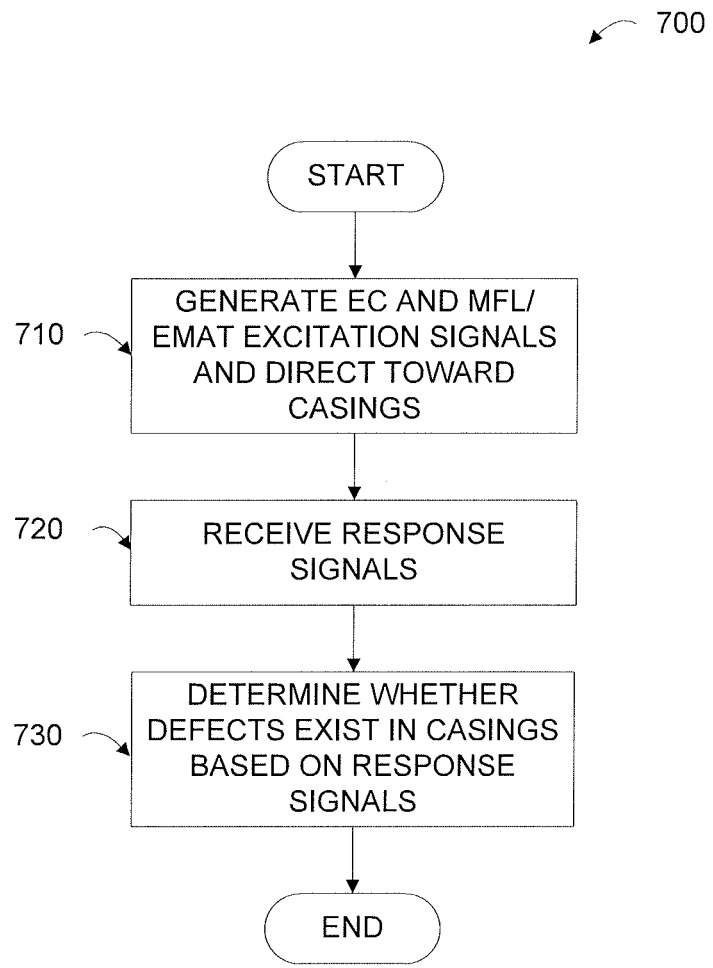
FIG. 7 illustrates an example method for performing wellbore casing evaluation using EC, MFL, or EMAT techniques in accordance with embodiments of the present disclosure.

FIG. 7 illustrates an example method 700 for performing wellbore casing evaluation using EC, MFL, or EMAT techniques, in accordance with embodiments of the present disclosure. The method begins at step 710, where excitation signals are generated and directed toward one or more wellbore casings for EC, MFL, and/or EMAT casing evaluation techniques. For example, generation of an excitation signal for EC techniques may include generating a transient electromagnetic fields using a coil (e.g., primary coil 401 of FIGS. 4A-4C), as described above. As another example, generation of an excitation signal for MFL techniques may include generating a static magnetic field using a coil (e.g., primary coil 401 of FIGS. 4A-4C) or a permanent magnet, as described above. As yet another example, generation of an excitation signal for EMAT techniques may include generating electromagnetic waves (e.g., an electromagnetic pulse) using a coil (e.g., secondary coil 406 of FIG. 4B), as described above.

At step 720, response signals are received. The response signals may be received in response to generation of the excitation signals in step 710. For example, response signals to EC excitation signals may include electromagnetic waves generated by eddy currents in the one or more casings caused by the excitation signal (i.e., static electromagnetic fields generated using a coil), as discussed above. Such response signals may be received by a coil, such as primary coil 401 in FIGS. 4A-4B or any other suitable coil or antenna. As another example, response signals to MFL excitation signals may include changes in the static magnetic field in a casing caused by defects. Such response signals may be received by magnetometers in close proximity to the casing, such as magnetometer 404 of FIG. 4A. As yet another example, response signals to EMAT excitation signals may include electromagnetic waves reflected from the casing. Such response signals may be received by coils in close proximity to the casing, such as secondary coil 406 of FIG. 4B.

At step 730, based on the received response signals, it is determined whether defects exist in the wellbore casings. For example, the response signals in MFL and/or EMAT evaluation techniques may be used to determine whether defects exist in an inner casing of a plurality of concentric wellbore casings. As another example, the response signals in EC evaluation techniques may be used to determine whether defects exist in one or more of a plurality of concentric wellbore casings. In certain embodiments, EC, MFL, EMAT, or any combination thereof, may be used to determine whether defects exist in the inner casings of a plurality of concentric wellbore casings.

In particular embodiments, relevant data for EC, MFL, and EMAT techniques can be acquired along the axial and/or azimuthal directions. The data may be sampled over a limited portion of the casing and then processed. For example, the acquired data can be processed to determine electrical properties of the casings and/or to evaluate the integrity of the casings (e.g., to find metal loss regions or other defects). Some of the operations that can be applied on data acquired include but not limited to: filtering to reduce noise; averaging multiple sensor data to reduce noise; taking the difference or the ratio of multiple voltages to remove unwanted effects such as a common voltage drift due to temperature; other temperature correction schemes such as a temperature correction table; calibration to known/expected parameter values from an existing well log; and array processing (software focusing) of the data to achieve different depth of detection or vertical/azimuthal resolution.

Furthermore, data processing may consist of operations to convert the acquired responses from the EC, MFL, and EMAT techniques to numbers, properties, and other relevant dimensions of the casings. This processing may include the use of inversion schemes, including but not limited to comparing the acquired response with a response in a library or responses from a forward modeling code and an iterative numerical optimization problem is solved based on the difference between the two. A numerical model of the formation or casing may then be constructed for forward modeling and construction of a library in certain embodiments.

Effects due to the presence of sensor housing, pad structure, mutual coupling between sensors, mud, and cement can be corrected by using information known a priori on these parameters, or by solving for some or all of them during the inversion process. Since all of these effects are mainly additive, they can be removed using proper calibration schemes. Multiplicative (scaling) portion of the effects can be removed in the process of calibration to an existing log. All additive, multiplicative and any other non-linear effect can be solved for by including them in the inversion process as a parameter. Removal of such effects is well-known in EM well logging, and it will not be detailed here.

Modifications, additions, or omissions may be made to method 700 without departing from the scope of the present disclosure. For example, the order of the steps may be performed in a different manner than that described and some steps may be performed at the same time. Additionally, each individual step may include additional steps without departing from the scope of the present disclosure.

To provide illustrations of one or more embodiments of the present disclosure, the following examples are provided.

In one embodiment, a system comprises one or more first electromagnetic coils configured to generate and direct first excitation signals toward a plurality of casings in a wellbore and receive response signals based on the excitation signals. The system also comprises a magnetic field source configured to generate a static magnetic field in a particular casing of the plurality of casings and a magnetometer configured to receive response signals based on the static magnetic field in the particular casing. The system further comprises one or more processors configured to receive a first response signal from the one or more electromagnetic coils, receive a second response signal from the magnetometer, and determine, based on the first response signal and the second response signal, whether a defect exists in the plurality of casings.

In one or more aspects of the disclosed system, the plurality of casings are concentric and comprise an inner casing and outer casings, determining whether a defect exists on the inner casing of the plurality of casings is based on the second response signal, and determining whether a defect exists on outer casings of the plurality of casings is based on the first response signal. In one or more aspects of the disclosed system, determining whether a defect exists on the inner casing of the plurality of casings is further based on the first response signal.

In one or more aspects of the disclosed system, the magnetic field source comprises the one or more first electromagnetic coils. In one or more aspects of the disclosed system, the first excitation signals and the static magnetic field are generated using the same electromagnetic coil. In one or more aspects of the disclosed system, the first excitation signals and the static magnetic field are generated using different electromagnetic coils. In one or more aspects of the disclosed system, the magnetic field source comprises a permanent magnet.

In one or more aspects of the disclosed system, the magnetometer comprises one or more pick-up coils. In one or more aspects of the disclosed system, the magnetometer comprises one or more Hall-effect sensors.

In one or more aspects of the disclosed system, the system further comprises one or more second electromagnetic coils configured to generate and direct second excitation signals toward the particular casing and receive response signals based on the second excitation signals, and the one or more processors are further configured to receive a third response signal from the one or more second electromagnetic coils and determine whether a defect exists in the plurality of casings using the first response signal, the second response signal, and the third response signal.

In another embodiment, a method comprises generating and directing first excitation signals toward a plurality of casings in a wellbore using one or more first electromagnetic coils, receiving first response signals from the one or more first electromagnetic coils based on the first excitation signals, generating a static magnetic field in a particular casing of the plurality of casings using a magnetic field source, receiving second response signals from a magnetometer based on the static magnetic field in the particular casing, and determining, based on the first response signals and the second response signals, whether a defect exists in the plurality of casings.

In one or more aspects of the disclosed method, the plurality of casings are concentric and comprise an inner casing and outer casings, determining whether a defect exists on the inner casing of the plurality of casings is based on the second response signal, and determining whether a defect exists on outer casings of the plurality of casings is based on the first response signal. In one or more aspects of the disclosed method, determining whether a defect exists on the inner casing of the plurality of casings is further based on the first response signal.

In one or more aspects of the disclosed method, the magnetic field source comprises the one or more first electromagnetic coils. In one or more aspects of the disclosed method, the first excitation signals and the static magnetic field are generated using the same electromagnetic coil. In one or more aspects of the disclosed method, the first excitation signals and the static magnetic field are generated using different electromagnetic coils. In one or more aspects of the disclosed method, the magnetic field source comprises a permanent magnet.

In one or more aspects of the disclosed method, the magnetometer comprises one or more pick-up coils. In one or more aspects of the disclosed method, the magnetometer comprises one or more Hall-effect sensors.

In one or more aspects of the disclosed method, the method further comprises generating and directing second excitation signals toward the particular casing using one or more second electromagnetic coils, receiving third response signals from the one or more second electromagnetic coils based on the second excitation signals, and determining whether a defect exists in the plurality of casings using the first response signal, the second response signal, and the third response signal.

In another embodiment, a system comprises one or more first electromagnetic coils configured to generate and direct first excitation signals toward a plurality of casings in a wellbore and receive response signals based on the first excitation signals. The system also comprises one or more second electromagnetic coils configured to generate and direct second excitation signals toward a particular casing of the plurality of casings and receive response signals based on the second excitation signals. The system further comprises one or more processors configured to receive a first response signal from the one or more first electromagnetic coils, receive a second response signal from the one or more second electromagnetic coils, and determine, based on the first response signal and the second response signal, whether a defect exists in the plurality of casings in the wellbore.

In one or more aspects of the disclosed system, the second excitation signals include electromagnetic pulses. In one or more aspects of the disclosed system, the spectral range of the electromagnetic pulses is within the range of 100 KHz and 10 MHz.

In one or more aspects of the disclosed system, the plurality of casings are concentric and comprise an inner casing and outer casings, determining whether a defect exists on the inner casing of the plurality of casings is based on the second response signal, and determining whether a defect exists on outer casings of the plurality of casings is based on the first response signal. In one or more aspects of the disclosed system, determining whether a defect exists on the inner casing of the plurality of casings is further based on the first response signal.

In one or more aspects of the disclosed system, the one or more first electromagnetic coils are the same as the one or more second electromagnetic coils. In one or more aspects of the disclosed system, the one or more first electromagnetic coils are different from the one or more second electromagnetic coils.

In one or more aspects of the disclosed system, the system further comprises a magnetic field source configured to generate a static magnetic field in the particular casing of the plurality of casings. In one or more aspects of the disclosed system, the magnetic field source comprises the one or more first electromagnetic coils. In one or more aspects of the disclosed system, the magnetic field source comprises a permanent magnet. In one or more aspects of the disclosed system, the system further comprises a magnetometer configured to receive response signals based on the static magnetic field in the particular casing, and the one or more processors are further configured to receive a third response signal from the magnetometer and determine whether a defect exists in the plurality of casings using the first response signal, the second response signal, and the third response signal.

In another embodiment, a method comprises generating and directing first excitation signals toward a plurality of casings in a wellbore using one or more first electromagnetic coils, and receiving first response signals from the one or more first electromagnetic coils based on the first excitation signals, generating and directing second excitation signals toward a particular casing of the plurality of casings using one or more second electromagnetic coils, receiving second response signals from the one or more second electromagnetic coils based on the second excitation signals; and determining, based on the first response signals and the second response signals, whether a defect exists in the plurality of casings.

In one or more aspects of the disclosed method, the second excitation signals include electromagnetic pulses. In one or more aspects of the disclosed method, the spectral range of the electromagnetic pulses is within the range of 100 KHz and 10 MHz.

In one or more aspects of the disclosed method, the plurality of casings are concentric and comprise an inner casing and outer casings, determining whether a defect exists on the inner casing of the plurality of casings is based on the second response signal, and determining whether a defect exists on outer casings of the plurality of casings is based on the first response signal. In one or more aspects of the disclosed method, determining whether a defect exists on the inner casing of the plurality of casings is further based on the first response signal.

In one or more aspects of the disclosed method, the one or more first electromagnetic coils are the same as the one or more second electromagnetic coils. In one or more aspects of the disclosed method, the one or more first electromagnetic coils are different from the one or more second electromagnetic coils.

In one or more aspects of the disclosed method, the method further comprises generating a static magnetic field in the particular casing of the plurality of casings using a magnetic field source. In one or more aspects of the disclosed method, the magnetic field source comprises the one or more first electromagnetic coils. In one or more aspects of the disclosed method, the magnetic field source comprises a permanent magnet. In one or more aspects of the disclosed method, the method further comprises receiving third response signals from a magnetometer based on the static magnetic field in the particular casing and determining whether a defect exists in the plurality of casings using the first response signal, the second response signal, and the third response signal.

The terms "couple" or "couples" as used herein are intended to mean either an indirect or a direct connection. Thus, if a first device couples to a second device, that connection may be through a direct connection, or through an indirect electrical or mechanical connection via other devices and connections. The term "uphole" as used herein means along the drill string or the hole from the distal end towards the surface, and "downhole" as used herein means along the drill string or the hole from the surface towards the distal end.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such as wires.

The present disclosure is well adapted to attain the ends and advantages mentioned, as well as those that are inherent therein. The particular embodiments disclosed herein are illustrative only, as the present disclosure may be modified and practiced in different but equivalent manners apparent to those skilled in the art having the benefit of the teachings herein. In the interest of clarity, not all features of an actual implementation may be described in this specification. It will of course be appreciated that in the development of any actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

What is claimed is:

1. A system, comprising:
one or more first electromagnetic coils configured to:
generate and direct first excitation signals toward a plurality of concentric casings in a wellbore, wherein the one or more first electromagnetic coils are placed at axial positions along at least one of the plurality of concentric casings; and
receive response signals based on the excitation signals;
a magnetic field source configured to generate a static magnetic field in a particular casing of the plurality of concentric casings;
a magnetometer configured to receive response signals based on the static magnetic field in the particular casing; and
one or more processors configured to:
receive a first response signal from the one or more electromagnetic coils;
receive a second response signal from the magnetometer; and
determine, based on the first response signal and the second response signal, whether a defect exists in the plurality of concentric casings.

2. The system of claim 1, wherein:
the plurality of concentric casings comprise an inner casing and outer casings;
determining whether a defect exists on the inner casing of the plurality of concentric casings is based on the second response signal; and
determining whether a defect exists on outer casings of the concentric plurality of casings is based on the first response signal.

3. The system of claim 2, wherein determining whether a defect exists on the inner casing of the plurality of concentric casings is further based on the first response signal.

4. The system of claim 1, wherein the magnetic field source comprises the one or more first electromagnetic coils.

5. The system of claim 4, wherein the first excitation signals and the static magnetic field are generated using the same electromagnetic coil.

6. The system of claim 4, wherein the first excitation signals and the static magnetic field are generated using different electromagnetic coils.

7. The system of claim 1, wherein the magnetic field source comprises a permanent magnet.

8. The system of claim 1, wherein the magnetometer comprises one or more pick-up coils.

9. The system of claim 1, wherein the magnetometer comprises one or more Hall-effect sensors.

10. The system of claim 1, wherein:
the system further comprises one or more second electromagnetic coils configured to:
generate and direct second excitation signals toward the particular casing; and
receive response signals based on the second excitation signals;
the one or more processors are further configured to:
receive a third response signal from the one or more second electromagnetic coils; and
determine whether a defect exists in the plurality of concentric casings using the first response signal, the second response signal, and the third response signal.

11. A method, comprising:
generating and directing first excitation signals toward a plurality of concentric casings in a wellbore using one or more first electromagnetic coils, wherein the one or more first electromagnetic coils are placed at axial positions along at least one of the plurality of concentric casings; and
receiving first response signals from the one or more first electromagnetic coils based on the first excitation signals;
generating a static magnetic field in a particular casing of the plurality of concentric casings using a magnetic field source;
receiving second response signals from a magnetometer based on the static magnetic field in the particular casing; and
determining, based on the first response signals and the second response signals, whether a defect exists in the plurality of concentric casings.

12. The method of claim 11, wherein:
the plurality of concentric casings comprise an inner casing and outer casings;
determining whether a defect exists on the inner casing of the plurality of concentric casings is based on the second response signal; and
determining whether a defect exists on outer casings of the plurality of concentric casings is based on the first response signal.

13. The method of claim 12, wherein determining whether a defect exists on the inner casing of the plurality of concentric casings is further based on the first response signal.

14. The method of claim 11, wherein the magnetic field source comprises the one or more first electromagnetic coils.

15. The method of claim 14, wherein the first excitation signals and the static magnetic field are generated using the same electromagnetic coil.

16. The method of claim 14, wherein the first excitation signals and the static magnetic field are generated using different electromagnetic coils.

17. The method of claim 11, wherein the magnetic field source comprises a permanent magnet.

18. The method of claim 11, wherein the magnetometer comprises one or more pick-up coils.

19. The method of claim 11, wherein the magnetometer comprises one or more Hall-effect sensors.

20. The method of claim 11, further comprising:
generating and directing second excitation signals toward the particular casing using one or more second electromagnetic coils;
receiving third response signals from the one or more second electromagnetic coils based on the second excitation signals; and determining whether a defect exists in the plurality of concentric casings using the first response signal, the second response signal, and the third response signal.

21. A system, comprising:
one or more first electromagnetic coils configured to:
generate and direct first excitation signals toward a plurality of concentric casings in a wellbore, wherein the one or more first electromagnetic coils are placed at axial positions along at least one of the plurality of concentric casings; and
receive response signals based on the first excitation signals;
one or more second electromagnetic coils configured to:
generate and direct second excitation signals toward a particular casing of the plurality of concentric casings; and
receive response signals based on the second excitation signals;
one or more processors configured to:
receive a first response signal from the one or more first electromagnetic coils;
receive a second response signal from the one or more second electromagnetic coils; and
determine, based on the first response signal and the second response signal, whether a defect exists in the plurality of concentric casings in the wellbore.

22. The system of claim 21, wherein the second excitation signals include electromagnetic pulses.

23. The system of claim 22, wherein the spectral range of the electromagnetic pulses is within the range of 100 KHz and 10 MHz.

24. The system of claim 21, wherein:
the plurality of concentric casings comprise an inner casing and outer casings;
determining whether a defect exists on the inner casing of the plurality of concentric casings is based on the second response signal; and
determining whether a defect exists on outer casings of the plurality of concentric casings is based on the first response signal.

25. The system of claim 24, wherein determining whether a defect exists on the inner casing of the plurality of concentric casings is further based on the first response signal.

26. The system of claim 21, wherein the one or more first electromagnetic coils are the same as the one or more second electromagnetic coils.

27. The system of claim 21, wherein the one or more first electromagnetic coils are different from the one or more second electromagnetic coils.

28. The system of claim 21, wherein the system further comprises a magnetic field source configured to generate a static magnetic field in the particular casing of the plurality of concentric casings.

29. The system of claim 28, wherein the magnetic field source comprises the one or more first electromagnetic coils.

30. The system of claim 28, wherein the magnetic field source comprises a permanent magnet.

31. The system of claim 28, wherein:
the system further comprises a magnetometer configured to receive response signals based on the static magnetic field in the particular casing; and the one or more processors are further configured to:
receive a third response signal from the magnetometer; and
determine whether a defect exists in the plurality of concentric casings using the first response signal, the second response signal, and the third response signal.

32. A method, comprising:
generating and directing first excitation signals toward a plurality of concentric casings in a wellbore using one or more first electromagnetic coils, wherein the one or more first electromagnetic coils are placed at axial positions along at least one of the plurality of concentric casings; and
receiving first response signals from the one or more first electromagnetic coils based on the first excitation signals;
generating and directing second excitation signals toward a particular casing of the plurality of concentric casings using one or more second electromagnetic coils; and
receiving second response signals from the one or more second electromagnetic coils based on the second excitation signals;
determining, based on the first response signals and the second response signals, whether a defect exists in the plurality of concentric casings.

33. The method of claim 32, wherein the second excitation signals include electromagnetic pulses.

34. The method of claim 33, wherein the spectral range of the electromagnetic pulses is within the range of 100 KHz and 10 MHz.

35. The method of claim 32, wherein:
the plurality of concentric casings comprise an inner casing and outer casings;
determining whether a defect exists on the inner casing of the plurality of concentric casings is based on the second response signal; and
determining whether a defect exists on outer casings of the plurality of concentric casings is based on the first response signal.

36. The method of claim 35, wherein determining whether a defect exists on the inner casing of the plurality of concentric casings is further based on the first response signal.

37. The method of claim 32, wherein the one or more first electromagnetic coils are the same as the one or more second electromagnetic coils.

38. The method of claim 32, wherein the one or more first electromagnetic coils are different from the one or more second electromagnetic coils.

39. The method of claim 32, further comprising generating a static magnetic field in the particular casing of the plurality of concentric casings using a magnetic field source.

40. The method of claim 39, wherein the magnetic field source comprises the one or more first electromagnetic coils.

41. The method of claim 39, wherein the magnetic field source comprises a permanent magnet.

42. The method of claim 39, further comprising:
receiving third response signals from a magnetometer based on the static magnetic field in the particular casing; and
determining whether a defect exists in the plurality of concentric casings using the first response signal, the second response signal, and the third response signal.

* * * * *